(12) United States Patent
El-Nounou et al.

(10) Patent No.: US 8,641,666 B2
(45) Date of Patent: Feb. 4, 2014

(54) CATHETER WITH LAMINAR FLOW DRUG DELIVERY PROPERTIES

(75) Inventors: Fozan O. El-Nounou, Santa Clara, CA (US); Florian N. Ludwig, Mountain View, CA (US); Syed F. A. Hossainy, Fremont, CA (US); Paul Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1052 days.

(21) Appl. No.: 11/749,665

(22) Filed: May 16, 2007

(65) Prior Publication Data

US 2008/0287911 A1 Nov. 20, 2008

(51) Int. Cl.
*A61M 29/00* (2006.01)
*A61M 31/00* (2006.01)

(52) U.S. Cl.
USPC ............. 604/107; 604/508; 604/103.02

(58) Field of Classification Search
USPC ........... 604/95.05, 103.01, 103.02, 103.07, 604/103.08, 103.09, 107, 158
See application file for complete search history.

(56) References Cited

U.S. PATENT DOCUMENTS

| | | | | |
|---|---|---|---|---|
| 4,802,650 A * | 2/1989 | Stricker | | 251/117 |
| 5,437,638 A | 8/1995 | Bowman | | |
| 5,584,872 A * | 12/1996 | LaFontaine et al. | | 607/116 |
| 5,713,853 A * | 2/1998 | Clark et al. | | 604/509 |
| 5,747,058 A * | 5/1998 | Tipton et al. | | 424/423 |
| 5,833,682 A * | 11/1998 | Amplatz et al. | | 606/15 |
| 5,876,426 A * | 3/1999 | Kume et al. | | 607/88 |
| 5,902,328 A * | 5/1999 | LaFontaine et al. | | 607/116 |
| 5,904,670 A * | 5/1999 | Schreiner | | 604/523 |
| 5,964,751 A * | 10/1999 | Amplatz et al. | | 606/15 |
| 6,117,125 A * | 9/2000 | Rothbarth et al. | | 604/523 |
| 6,171,275 B1 * | 1/2001 | Webster, Jr. | | 604/20 |
| 6,217,554 B1 * | 4/2001 | Green | | 604/164.01 |
| 6,261,255 B1 | 7/2001 | Mullis et al. | | |
| 6,263,236 B1 * | 7/2001 | Kasinkas et al. | | 604/21 |
| 6,280,413 B1 * | 8/2001 | Clark et al. | | 604/104 |
| 6,364,894 B1 | 4/2002 | Healy et al. | | |
| 6,676,900 B1 | 1/2004 | Divino, Jr. et al. | | |
| 6,702,783 B1 | 3/2004 | Dae et al. | | |
| 6,786,884 B1 | 9/2004 | DeCant, Jr. et al. | | |
| 6,958,059 B2 * | 10/2005 | Zadno-Azizi | | 604/509 |
| 6,984,232 B2 * | 1/2006 | Vanney et al. | | 606/41 |
| 6,990,982 B1 * | 1/2006 | Bonutti | | 128/898 |
| 7,077,822 B1 * | 7/2006 | Howard, III | | 604/93.01 |
| 7,438,714 B2 * | 10/2008 | Phan | | 606/49 |
| 7,470,252 B2 * | 12/2008 | Mickley et al. | | 604/103.02 |
| 8,007,470 B2 * | 8/2011 | Shirley et al. | | 604/164.01 |
| 2002/0055717 A1 | 5/2002 | Poncet | | |
| 2002/0136694 A1 | 9/2002 | Wallingford et al. | | |

(Continued)

FOREIGN PATENT DOCUMENTS

| | | |
|---|---|---|
| WO | WO 97/36633 | 10/1997 |
| WO | WO 02/058768 | 8/2002 |

OTHER PUBLICATIONS

International Search Report for PCT/US2008/061050, mailed Jul. 30, 2008, 17 pgs.

*Primary Examiner* — Kevin C Sirmons
*Assistant Examiner* — Andrew Gilbert
(74) *Attorney, Agent, or Firm* — Squire Sanders (US) LLP

(57) ABSTRACT

Catheters with laminar flow bioactive agent delivery properties and methods of using for treating or preventing vascular disease are disclosed.

15 Claims, 3 Drawing Sheets

(56) References Cited

U.S. PATENT DOCUMENTS

| | | |
|---|---|---|
| 2003/0211123 A1* | 11/2003 | Shukla et al. ................. 424/400 |
| 2003/0216685 A1 | 11/2003 | Porter |
| 2004/0158276 A1 | 8/2004 | Barbut et al. |
| 2005/0107817 A1 | 5/2005 | White et al. |
| 2006/0004399 A1 | 1/2006 | van Ockenburg et al. |
| 2007/0250035 A1* | 10/2007 | El-Nounou et al. .......... 604/509 |
| 2008/0097297 A1* | 4/2008 | Kelley et al. ............. 604/103.01 |

* cited by examiner

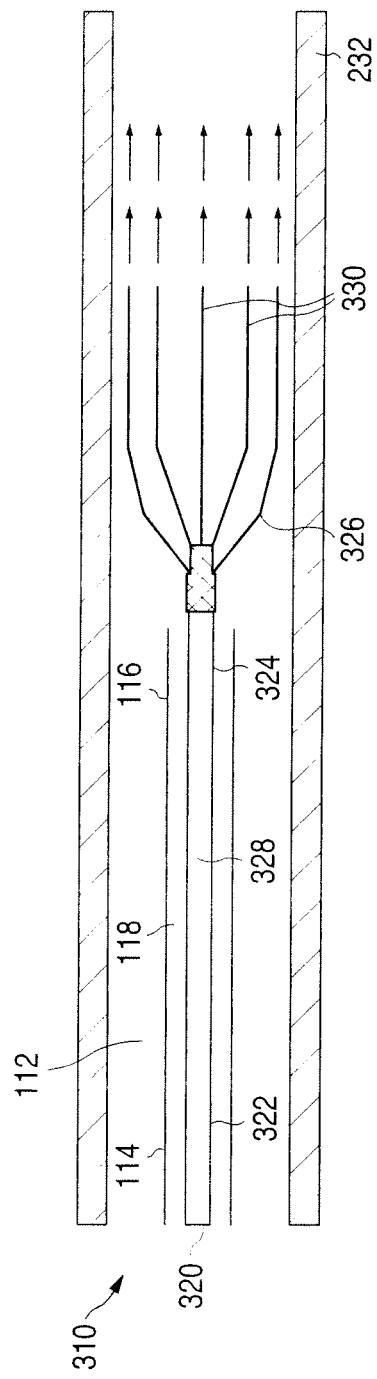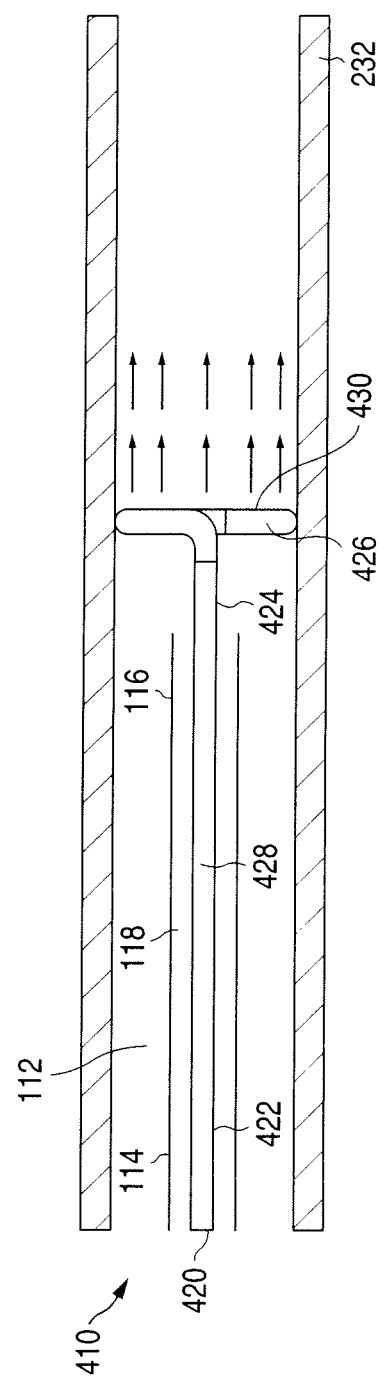

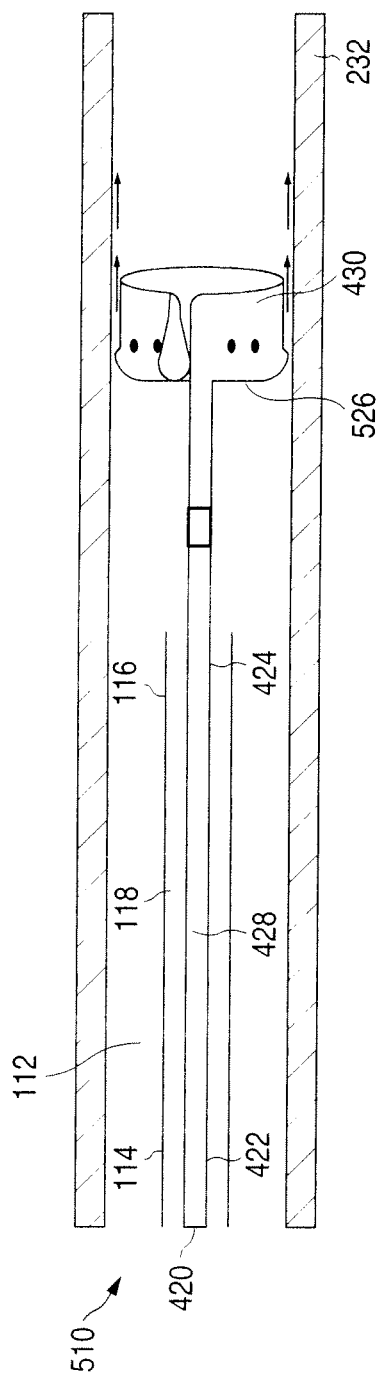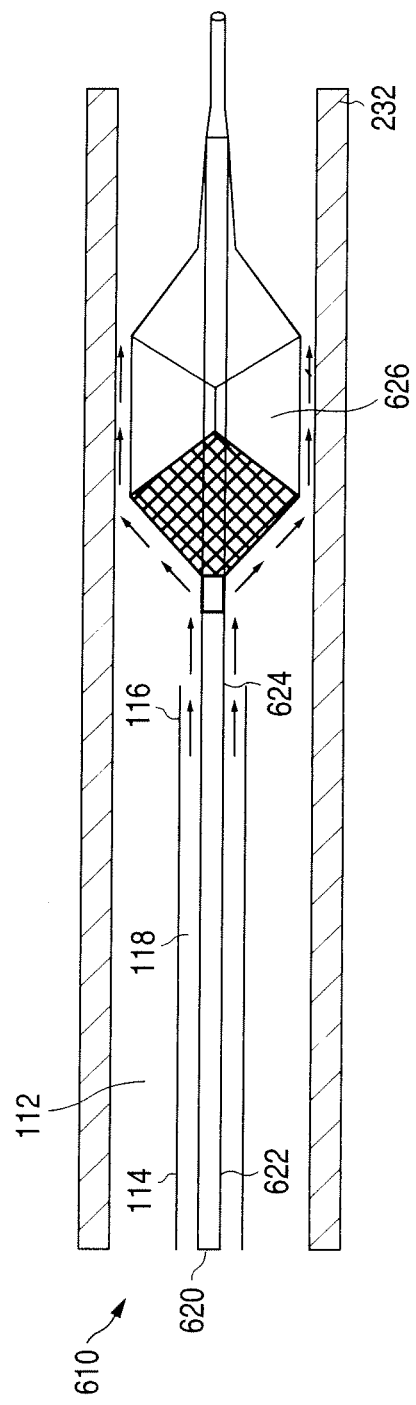

CATHETER WITH LAMINAR FLOW DRUG DELIVERY PROPERTIES

FIELD OF THE INVENTION

This present invention relates to a catheter with laminar flow drug delivery properties and methods of using for the treatment of vascular disease.

BACKGROUND OF THE INVENTION

The traditional method of administering therapeutic agents to treat diseases of the internal organs and vasculature has been by systemic delivery. Systemic delivery involves administering a therapeutic agent at a discrete location followed by the agent migrating throughout the patient's body including, of course, to the afflicted organ or area of the vasculature. But to achieve a therapeutic amount of the agent at the afflicted site, an initial dose substantially greater than the therapeutic amount must be administered to account for the dilution the agent undergoes as it travels through the body.

At the other end of the spectrum is local delivery, which comprises administering the therapeutic agent directly to the afflicted site. With localized delivery the initial dose can be at or very close to the therapeutic amount. With time, some of the locally delivered therapeutic agent may diffuse over a wider region, but that is not the intent of localized delivery, and the diffused agent's concentration will ordinarily be sub-therapeutic, i.e., too low to have a therapeutic effect. Nevertheless, localized delivery of therapeutic agents is currently considered a state-of-the-art approach to the treatment of many diseases such as cancer and atherosclerosis.

Localized delivery of therapeutic agents can consist of administering a composition containing a therapeutic agent and a targeting moiety designed to interact specifically with a biochemical entity present at, and exclusive to, the afflicted site in the vasculature. A means to administer the compositions without losing a substantial fraction to the systemic circulation or a means to preferentially localize composition components to an endothelium is, however, lacking in the art.

The present invention provides catheter assemblies for delivering therapeutic compositions to an endothelium and methods of using the assemblies for the treatment of vascular disease.

SUMMARY OF THE INVENTION

The present invention relates to a catheter that includes an elongate tubular member including a proximal end, a distal end and a lumen extending from the proximal end to the distal end and an elongate cylindrical member disposed at least partially within the lumen of the elongate tubular member along the longitudinal axis of symmetry and having a proximal end, a distal end and a delivery assembly extending from the distal end. The delivery assembly is capable of producing a laminar flow of a bioactive agent formulation at or near a blood vessel wall in which the catheter is disposed.

In various aspects of the invention, the elongate cylindrical member can be extendable and retractable such that in its retracted position the delivery assembly can be disposed within the lumen of the tubular member and in its extendable position the delivery assembly extends beyond the distal end of the tubular member.

In one aspect of the invention, the delivery assembly includes a flared conical shaped solid member when the elongate cylindrical member is in its extendable position.

In various aspects of the invention, the elongate cylindrical member includes a lumen extending from the proximal end to the distal end of the elongate cylindrical member.

In one aspect of the invention, the elongate cylindrical member lumen opens to a plurality of tubular channels radiating outward from the distal end of the elongate cylindrical member through the delivery assembly where they open to the blood vessel. The delivery assembly includes a flared conical shaped member, within which the plurality of tubular channels are disposed when the elongate cylindrical member is in its extendable position.

In one aspect of the invention, the elongate cylindrical member lumen opens to a delivery assembly that includes a plurality of tubular extensions open to the blood vessel. Each tubular extension is positioned near or in contact with the wall of a blood vessel when the elongate cylindrical member is in its extendable position.

In one aspect of the invention, the elongate cylindrical member lumen opens to a delivery assembly that includes a ring element oriented perpendicular to the lumen when the elongate cylindrical member is in its extendable position. In one embodiment, the ring element includes a plurality of holes positioned along the down-stream side of the ring element. In another embodiment, the ring element includes an air foil-shaped configuration and includes a plurality of holes positioned along the abluminal side of the ring element. In further embodiments, the ring element is self-expanding, can include a shape memory polymer or can include a shape memory metal.

In one aspect of the invention, the delivery assembly includes a flared sieve when the elongate cylindrical member is in its extendable position. In one embodiment, the sieve is self-expanding. In another embodiment, the sieve is balloon-expandable.

In various aspects of the invention, the delivery assembly is made of a shape memory polymer or a shape memory metal. In one embodiment, it can be nitinol.

Another aspect of the present invention relates to a method for treating or preventing a vascular disease. The method involves providing a catheter according to the invention, inserting the catheter into the blood vessel of a patient, providing a bioactive agent formulation and introducing the bioactive agent formulation into the blood vessel of a patient through the catheter. In one embodiment, the bioactive agent formulation has a viscosity higher than that of blood.

In one aspect of the invention, the viscosity of the bioactive agent formulation is modified by an excipient that can include a polymer, a protein, a sugar or an alcohol.

In one aspect of the invention, introducing the bioactive agent formulation into the blood vessel of a patient does not impede the flow of blood through the vessel.

In various aspects of the invention, the bioactive agent formulation can include a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, an antifibrotic agent, a profibrotic agent, an antithrombotic agent, a matrix metalloproteinase inhibitor or a tissue inhibitor of metalloproteinase.

BRIEF DESCRIPTION OF THE DRAWINGS

FIG. 3 depicts a cross-sectional view of a catheter that includes a delivery assembly that includes a plurality of tubular extensions open to the blood vessel.

FIG. 4 depicts a cross-sectional view of a catheter that includes a delivery assembly that includes a ring element oriented perpendicular to a lumen and includes holes positioned along the down-stream side of the element.

FIG. 5A depicts a cross-sectional view of a catheter that includes a delivery assembly that includes an air foil-shaped ring element oriented perpendicular to a lumen and includes holes positioned along the abluminal side of the ring element. FIGS. 5B-C depict cross-sectional illustrations of various ring element embodiments of FIG. 5A.

FIG. 6 depicts a cross-sectional view of a catheter that includes a delivery assembly that includes a flared sieve.

DETAILED DESCRIPTION OF THE INVENTION

Figure 1:
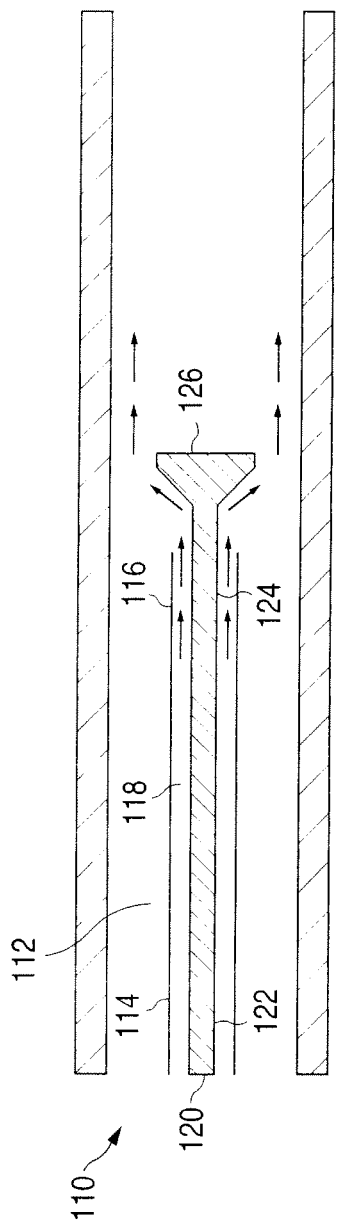
FIG. 1 depicts a cross-sectional view of a catheter that includes a delivery assembly with a flared conical shaped solid member.

The present invention provides catheters capable of producing laminar or near-laminar flow of a bioactive agent formulation at or near the wall of a blood vessel. The catheter designs minimize bioactive agent wash out into the blood circulation, allow blood to flow naturally and unimpeded during bioactive agent formulation delivery and allow efficient bioactive agent uptake by endothelium. By controlling bioactive agent formulation viscosity, density and flow rate, laminar flow can be achieved thereby providing an effective means for treating vascular disease.

Definitions:

As used herein, "lumen" refers to a cavity of a tubular structure including an organ such as a blood vessel or a device such as a catheter.

As used herein, "laminar flow" refers to the flow of a fluid when it flows in parallel layers without disruption between the layers. Fluids exhibit laminar flow near a solid boundary.

As used herein, "near-laminar flow" refers to the flow of a fluid when it flows in parallel layers with minimal disruption between the layers.

As used herein, "viscosity" refers to the property of a fluid to resist flow.

As used herein, "sieve" refers to a structure that is capable of allowing certain materials to pass through it while preventing other materials from passing through it.

As used herein, the term "flared" refers to the shape of a structure that opens or spreads outwardly.

As used herein, a "bioactive agent" refers to any substance that is of medical or veterinary therapeutic, diagnostic or prophylactic utility.

A therapeutic bioactive agent further refers to a bioactive agent that, when administered in a therapeutically effective amount to a patient suffering from a disease, has a therapeutic beneficial effect on the health and well-being of the patient. A therapeutic beneficial effect on the health and well-being of a patient includes, but it not limited to: (1) curing the disease; (2) slowing the progress of the disease; (3) causing the disease to regress; or (4) alleviating one or more symptoms of the disease.

A bioactive agent also refers to an agent that, when administered to a patient, either prevents the occurrence of a disease or disorder or retards the recurrence of the disease or disorder. Such a bioactive agent may be referred to as a prophylactic bioactive agent.

Suitable antiproliferative agents include, without limitation, actinomycin D, or derivatives or analogs thereof, i.e., actinomycin D is also known as dactinomycin, actinomycin IV, actinomycin $I_1$, actinomycin $X_1$, and actinomycin $C_1$. Antiproliferative agents can be natural proteineous agents such as a cytotoxin or a synthetic molecule, all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin, prodrugs thereof, co-drugs thereof, and combinations thereof.

Suitable anti-inflammatory agents include, without limitation, steroidal anti-inflammatory agents, a nonsteroidal anti-inflammatory agent, or a combination thereof In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof The anti-inflammatory agent may also be a biological inhibitor of proinflammatory signaling molecules including antibodies to such biological inflammatory signaling molecules.

Suitable antineoplastics and/or antimitotics include, without limitation, paclitaxel, docetaxel, methotrexate, azathioprine, vincristine, vinblastine, fluorouracil, doxorubicin hydrochloride, and mitomycin.

Suitable antiplatelet, anticoagulant, antifibrin, and antithrombin drugs include, without limitation, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as Angiomax ä (Biogen, Inc., Cambridge, Mass.), calcium channel blockers (such as nifedipine), colchicine, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.).

Suitable cytostatic or antiproliferative agents include, without limitation, angiopeptin, angiotensin converting enzyme inhibitors such as captopril, cilazapril or lisinopril, calcium channel blockers such as nifedipine; colchicine, fibroblast growth factor (FGF) antagonists; fish oil (ω-3-fatty acid); histamine antagonists; lovastatin, monoclonal antibodies such as, without limitation, those specific for Platelet-Derived Growth Factor (PDGF) receptors; nitroprusside, phosphodiesterase inhibitors, prostaglandin inhibitors, suramin, serotonin blockers, steroids, thioprotease inhibitors, triazolopyrimidine (a PDGF antagonist) and nitric oxide. Suitable antiallergic agents include, without limitation, permirolast potassium.

Other suitable bioactive agents include, without limitation, alpha-interferon, genetically engineered epithelial cells, synthetic inorganic and organic compounds, proteins and peptides, polysaccharides and other sugars, lipids, and DNA and RNA nucleic acid sequences having therapeutic, prophylactic or diagnostic activities, nucleic acid sequences include genes, antisense molecules which bind to complementary DNA to inhibit transcription, and ribozymes. Some other examples of suitable bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy; antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents.

Preferred bioactive agents include a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, an antifibrotic agent, a profibrotic agent, an antithrombotic agent, a matrix metalloproteinase inhibitor or a tissue inhibitor of metalloproteinase.

The amount of bioactive agent in a bioactive agent formulation will depend on the required minimum effective concentration (MEC) of the agent and the length of time over which it is desired that the MEC be maintained. For most bioactive agents the MEC will be known to, or readily derivable by, those skilled in the art. For experimental bioactive agents or those for which the MEC by localized delivery is not known, the MEC can be empirically determined using techniques well-known to those skilled in the art.

As used herein, a "patient" refers to any organism that can benefit from the administration of a bioactive agent. In particular, patient refers to a mammal such as a cat, dog, horse, cow, pig, sheep, rabbit, goat or a human being.

As used herein, "treating" refers to the administration of a therapeutically effective amount of a bioactive agent to a patient known or suspected to be suffering from a vascular disease. Bioactive agents useful with this invention are described above.

As used herein, a "therapeutically effective amount" refers to the amount of bioactive agent that has a beneficial effect, which may be curative or palliative, on the health and well-being of a patient with regard to a vascular disease with which the patient is known or suspected to be afflicted. A therapeutically effective amount may be administered as a single bolus, as intermittent bolus charges, as short, medium or long term sustained release formulations or as any combination of these.

As used herein, "known" to be afflicted with a vascular disease refers first to a condition that is relatively readily observable and or diagnosable. An example, without limitation, of such a disease is atherosclerosis, which is a discrete narrowing of a patient's arteries. Restenosis, on the other hand, while in its latter stages, like atherosclerosis, is relatively readily diagnosable or directly observable, may not be so in its nascent stage. Thus, a patient may be "suspected" of being afflicted or of being susceptible to affliction with restenosis at some time subsequent to a surgical procedure to treat an atherosclerotic lesion.

As used herein, a "vascular disease locale" refers to the location within a patient's body where an atherosclerotic lesion(s) is present, where restenosis may develop, the site of vulnerable plaque(s) or the site of a peripheral arterial disease.

As used herein, an "atherosclerotic lesion" refers to a deposit of fatty substances, cholesterol, cellular waste products, calcium and/or fibrin on the inner lining or intima of an artery.

As used herein, "restenosis" refers to the re-narrowing or blockage of an artery at or near the site where angioplasty or another surgical procedure was previously performed to remove a stenosis.

Vulnerable plaque on the other hand is quite different from either atherosclerosis or restenosis. Vulnerable plaque occurs primarily within the wall of a vessel and does not cause prominent protrusions into the lumen of the vessel. It is often not until it is "too late," i.e., until after a vulnerable plaque has broken and released its components into the vessel, that its presence is even known. Numerous methods have and are being investigated for the early diagnosis of vulnerable plaque but to date none have proven completely successful.

As used herein, a "peripheral arterial disease" refers to a condition similar to coronary artery disease and carotid artery disease in which fatty deposits build up in the inner linings of the artery walls thereby restricting blood circulation, mainly in arteries leading to the kidneys, stomach, arms, legs and feet.

As used herein, "bioactive agent formulation" refers to a composition that includes a bioactive agent of the invention and can further include an excipient of the invention.

As used herein, "excipient" refers to a chemically inert substance that can be used as a bioactive agent carrier.

FIG. 1 illustrates a catheter in accordance with one aspect of the invention. Catheter 110 includes elongate tubular member 112 that includes proximal end 114 and distal end 116. Elongate tubular member 112 also includes lumen 118 extending from proximal end 114 to distal end 116. Catheter 110 further includes elongate cylindrical member 120 which is disposed at least partially within the lumen of elongate tubular member 112 and includes proximal end 122, distal end 124 and delivery assembly 126 coupled to or extending from distal end 124. Elongate cylindrical member 120 can be extendable and retractable. In its retracted position, delivery assembly 126 is disposed within lumen 118 of elongate tubular member 112. In its extendable position, delivery assembly 126 extends beyond distal end 116 of elongate tubular member 112.

Catheter 110 provides a means for delivering a bioactive agent formulation at or near a blood vessel wall in which catheter 110 is disposed by producing a laminar flow of the bioactive agent formulation at or near the blood vessel wall. Laminar flow is possible due to the shape of delivery assembly 126. Specifically, delivery assembly 126 has a flared conical shaped solid member when elongate cyclindrical member 120 is in its extendable position, as shown in FIG. 1.

When Catheter 110 is positioned inside a blood vessel, the bioactive agent formulation can move from proximal end 114 to distal end 116 inside lumen 118 but along the outside of elongate cylindrical member 120. When the formulation arrives at delivery assembly 126 it is directed to the edges of the blood vessel by the flared conical shaped solid member of delivery assembly 126, as shown in FIG. 1.

After delivery to the blood vessel wall, the bioactive agent formulation's viscosity, density and rate at which it is administered will affect the ability of the bioactive formulation to undergo laminar flow.

Viscosity is a measure of a fluid's tendency to resist flow. The more viscous a fluid is, the harder it is to disrupt the layers of the fluid which enhances a fluid's ability to undergo laminar flow. In one embodiment of the present invention therefore, the bioactive agent formulation has a viscosity higher than that of blood. This allows the formulation to undergo laminar flow at or near a blood vessel wall, which in turn provides a means for the efficient delivery of bioactive agent to endothelium. The viscosity of the formulation can be modified by an excipient such as a polymer, a protein, a sugar or an alcohol, methods of which are known to those skilled in the art. Other suitable excipients include poly(ethylene glycol), polyvinyl pyrrolidone, bovine serum albumin, dextrane, poly (vinyl alcohol) and hyaluronic acid.

Density also affects a fluid's viscosity. The denser a fluid, the more viscous it is. Therefore, the density of the bioactive agent formulation will be controlled so that the viscosity of the formulation is higher than that of blood. Suitable viscosity values for the formulation range from 5 to 500 centipoise, preferably 5-50 centipoise.

The rate at which the bioactive agent formulation is administered via a catheter of the invention will also affect the ability to induce laminar flow of the formulation. At low Reynold's number, usually at low velocity, flow inside a vessel is laminar, and fluid flow remains virtually unmixed, with the layers of flow sliding along each other. In contrast, at a high Reynold's number, usually at higher velocities, the flow in the core of the vessel becomes turbulent with swirling eddies throughout. Therefore, the administration rate is controlled to help produce laminar flow of the bioactive agent formulation after delivery to a blood vessel wall via a catheter of the invention. Suitable administration rates range from 0.1 ml/min to 100 ml/min, preferably from 1 ml/min to 10 ml/min.

It is to be understood that the viscosity and density of the bioactive agent formulation as well as the rate at which it is administered can be individually tailored for each catheter of the invention so as to produce laminar flow of the bioactive agent formulation at or near a blood vessel wall in which the catheter is disposed.

Figure 2:
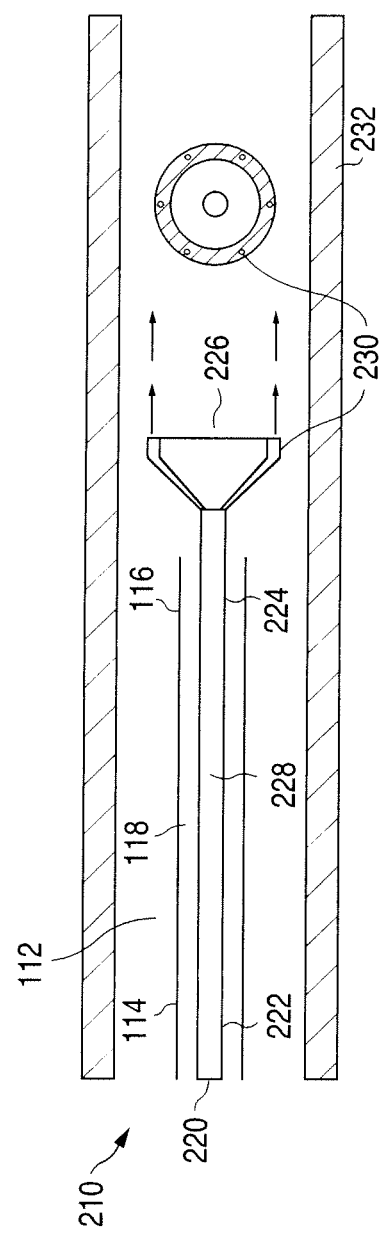
FIG. 2 depicts a cross-sectional view of a catheter that includes a delivery assembly with a flared conical shaped member that includes tubular channels open to a blood vessel.

FIG. 2 illustrates a catheter in accordance with another aspect of the invention. Catheter 210 includes elongate tubular member 112 that includes proximal end 114 and distal end 116. Elongate tubular member 112 also includes lumen 118 extending from proximal end 114 to distal end 116. Catheter 210 further includes elongate cylindrical member 220 which is disposed at least partially within lumen 118 of elongate tubular member 112 and includes proximal end 222, distal end 224 and delivery assembly 226 coupled to or extending from distal end 224 that includes a flared conical shaped member. Elongate cylindrical member 220 also includes lumen 228 extending from proximal end 222 to distal end 224. Lumen 228 opens to a plurality of tubular channels 230 radiating outward from distal end 224 of elongate cylindrical member 220 through delivery assembly 226 where they open to blood vessel 232. Delivery assembly 226 includes a flared conical shaped member within which the plurality of tubular channels 230 are disposed when elongate cylindrical member 220 is in its extendable position, as shown in FIG. 2.

Elongate cylindrical member 220 can be extendable and retractable. In its retracted position, delivery assembly 226 is disposed within lumen 118 of elongate tubular member 112. In its extendable position, delivery assembly 226 extends beyond distal end 116 of elongate tubular member 112.

Catheter 210 provides another means for delivering a bioactive agent formulation at or near blood vessel 232 wall in which catheter 210 is disposed by producing a laminar flow of the formulation at or near the blood vessel wall.

When catheter 210 is positioned inside blood vessel 232, the bioactive agent formulation will move within lumen 228 of elongate cylindrical member 220 from proximal end 222 to distal end 224 to delivery assembly 226. At delivery assembly 226, the bioactive agent formulation will move from lumen 228 into plurality of tubular channels 230 that radiate outward from distal end 224 through delivery assembly 226. This provides a means for inducing the bioactive agent formulation to undergo laminar flow at the vessel wall in which catheter 210 is disposed.

FIG. 3 illustrates a catheter in accordance with another aspect of the invention. Catheter 310 includes elongate tubular member 112 that includes proximal end 114 and distal end 116. Elongate tubular member 112 also includes lumen 118 extending from proximal end 114 to distal end 116. Catheter 310 further includes elongate cylindrical member 320 which is disposed at least partially within lumen 118 of elongate tubular member 112 and includes proximal end 322, distal end 324 and delivery assembly 326 coupled to or extending from distal end 324. Elongate cylindrical member 320 is preferably self-expanding, and can be extendable and retractable. In its retracted position, delivery assembly 326 is disposed within lumen 118 of elongate tubular member 112. In its extendable position, delivery assembly 326 extends beyond distal end 116 of elongate tubular member 112.

Elongate cylindrical member 320 also includes lumen 328 extending from proximal end 322 to distal end 324. Lumen 328 opens to delivery assembly 326 which includes plurality of tubular extensions 330 open to blood vessel 232. Each of tubular extensions 330 is positioned near or in contact with the wall of blood vessel 232 when elongate cylindrical member 320 is in its extendable position, as shown in FIG. 3. Tubular extensions 330 radially expand outwards such that their delivery ends are positioned about a generally circular pattern.

When catheter 310 is positioned inside blood vessel 232, the bioactive agent formulation can move within lumen 328 of elongate cylindrical member 320 from proximal end 322 to distal end 324 to delivery assembly 326. At delivery assembly 326, the bioactive agent formulation will move from lumen 328 into plurality of tubular extensions 330 which open to blood vessel 232 thereby providing a means for inducing the bioactive agent formulation to undergo laminar flow at the vessel wall in which catheter 310 is disposed.

FIG. 4 illustrates a catheter in accordance with another aspect of the invention. Catheter 410 includes elongate tubular member 112 that includes proximal end 114 and distal end 116. Elongate tubular member 112 also includes lumen 118 extending from proximal end 114 to distal end 116. Catheter 410 further includes elongate cylindrical member 420 which is disposed at least partially within lumen 118 of elongate tubular member 112 and includes proximal end 422, distal end 424 and delivery assembly 426 coupled to or extending from distal end 424. Elongate cylindrical member 420 can be extendable and retractable. In its retracted position, delivery assembly 426 is disposed within lumen 118 of elongate tubular member 112. In its extendable position, delivery assembly 426 extends beyond distal end 116 of elongate tubular member 112.

Elongate cylindrical member 420 also includes lumen 428 extending from proximal end 422 to distal end 424. Lumen 428 opens to delivery assembly 426 which includes a self-expanding ring element 430 oriented perpendicular to lumen 428 when elongate cylindrical member 420 is in its extendable position. Ring element 430 includes a plurality of holes positioned along the down-stream side of ring element 430 open to blood vessel 232, as shown in FIG. 4. Ring element 430 can include an embodiment of a closed ring or alternatively an open ring as illustrated in FIG. 4.

When catheter 410 is positioned inside blood vessel 232, the bioactive agent formulation can move within lumen 428 of elongate cylindrical member 420 from proximal end 422 to distal end 424 to delivery assembly 426. At delivery assembly 426, the bioactive agent formulation will move from lumen 428 into ring element 430 and out of the plurality of holes positioned along the down-stream side of ring element 430, thereby providing a means for inducing the bioactive agent formulation to undergo laminar flow at the vessel wall in which catheter 410 is disposed.

FIG. 5A illustrates a catheter in accordance with another aspect of the invention. Catheter 510 includes elongate tubular member 112 that includes proximal end 114 and distal end 116. Elongate tubular member 112 also includes lumen 118 extending from proximal end 114 to distal end 116. Catheter 510 further includes elongate cylindrical member 420 which is disposed at least partially within lumen 118 of elongate tubular member 112 and includes proximal end 422, distal end 424 and delivery assembly 526 coupled to or extending from distal end 424. Elongate cylindrical member 420 can be extendable and retractable. In its retracted position, delivery assembly 526 is disposed within lumen 118 of elongate tubular member 112. In its extendable position, delivery assembly 526 extends beyond distal end 116 of elongate tubular member 112.

Elongate cylindrical member 420 also includes lumen 428 extending from proximal end 422 to distal end 424. Lumen 428 opens to delivery assembly 526 which includes ring element 430 oriented perpendicular to lumen 428 when elongate cylindrical member 420 is in its extendable position. Delivery assembly 526 is preferably self-expanding and can include an air foil-shaped cross-sectional configuration (See FIG. 5B) and further includes a plurality of holes positioned along the abluminal side and open to blood vessel 232. FIG. 5C illustrates an alternative cross-sectional configuration in the shape of an airplane wing. Ring element 430 can include an open ring configuration as illustrated, to allow for ring element 430 to be easily pulled into and pushed out of lumen 118.

When catheter 510 is positioned inside blood vessel 232, the bioactive agent formulation can move within lumen 428 of elongate cylindrical member 420 from proximal end 422 to distal end 424 to delivery assembly 526. At delivery assembly 526, the bioactive agent formulation will move from lumen 428 into ring element 430 and out of the plurality of holes positioned along the abluminal side of ring element 430, thereby providing a means for inducing the bioactive agent formulation to undergo laminar flow at the vessel wall in which catheter 510 is disposed.

FIG. 6 illustrates a catheter in accordance with another aspect of the invention. Catheter 610 includes elongate tubular member 112 that includes proximal end 114 and distal end 116. Elongate tubular member 112 also includes lumen 118 extending from proximal end 114 to distal end 116. Catheter 610 further includes elongate cylindrical member 620 which is disposed at least partially within lumen 118 of elongate tubular member 112 and includes proximal end 622, distal end 624 and delivery assembly 626 coupled to or extending from distal end 624. Elongate cylindrical member 620 can be extendable and retractable. In its retracted position, delivery assembly 626 is disposed within lumen 118 of elongate tubular member 112. In its extendable position, delivery assembly 626 extends beyond distal end 116 of elongate tubular member 112.

Catheter 610 provides a means for delivering a bioactive agent formulation at or near a blood vessel wall in which catheter 610 is disposed by producing a laminar flow of the bioactive agent formulation at or near the blood vessel wall. Laminar flow is possible due to the shape of delivery assembly 626. Specifically, delivery assembly 626 comprises a flared sieve when elongate cylindrical member 620 is in its extendable position, as shown in FIG. 6.

When catheter 610 is positioned inside a blood vessel, bioactive agent formulation moves from proximal end 114 to distal end 116 inside lumen 118 but along the outside of elongate cylindrical member 620. When the formulation arrives at delivery assembly 626 it is directed to the edges of the vessel by the flared sieve of delivery assembly 626. The flared sieve directs bioactive agent formulation towards the wall of blood vessel 232 while allowing blood components, e.g., blood cells and platelets, to move through the sieve. In one embodiment, the flared sieve is self-expanding. In another embodiment, the flared sieve is balloon-expandable.

The above described delivery assemblies can be made from a shape memory polymer or a shape memory metal. This allows a delivery assembly to assume its normal or intended shape when it is in its extendable position. In a preferred embodiment, the delivery assembly can made from nitinol.

The present invention also relates to a method for treating or preventing a vascular disease. The method involves providing a catheter of the invention, inserting the catheter into the blood vessel of a patient, providing a bioactive agent formulation having a viscosity less than that of blood and introducing the bioactive agent formulation into the blood vessel of a patient through the catheter.

Methods of inserting a catheter into the blood vessel of a patient are known to those skilled in the art. It is to be understood that introducing the bioactive agent formulation into the blood vessel of a patient with any of the catheters of the invention does not impede the flow of blood through the vessel.

Vascular diseases that may be treated or prevented using a catheter and method of the present invention are described above.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

We claim:

1. A catheter comprising:
    an elongate tubular member comprising a proximal end, a distal end and a lumen extending from the proximal end to the distal end; and
    an elongate cylindrical member disposed at least partially within the lumen of the elongate tubular member and having a proximal end, a distal end and a delivery assembly extending from the distal end, wherein the delivery assembly comprises a flared conical shaped member, and wherein a fluid delivery lumen within the elongate cylindrical member opens to a plurality of tubular fluid delivery channels disposed within the flared conical shaped member,
    wherein the tubular fluid delivery channels are embedded within a wall of the flared conical shaped member, each of the tubular fluid delivery channels terminate at a fluid exit opening, each fluid exit opening is formed in the wall of the flared conical shaped member and discharges liquid received from the fluid delivery lumen out of the fluid exit opening to deliver a bioactive agent to a patient, and each fluid exit opening faces in a distal direction away from the distal end of the elongate cylindrical member.

2. The catheter according to claim 1, wherein the elongate cylindrical member is extendable and retractable such that in its retracted position the delivery assembly is disposed within the lumen of the tubular member and in its extended position the delivery assembly extends beyond the distal end of the tubular member.

3. The catheter according to claim 1, wherein the lumen of the elongate cylindrical member extends from the proximal end to the distal end of the elongate cylindrical member.

4. The catheter according to claim 2, wherein each of the plurality of tubular fluid delivery channels radiates outward from the distal end of the elongate cylindrical member when the elongate cylindrical member is in its extended position.

5. The catheter according to claim 2, wherein the delivery assembly comprises a shape memory polymer or a shape memory metal.

6. The catheter according claim 1, wherein the wall of the flared conical shaped member forms a circle, as viewed in line with a longitudinal axis of the elongate tubular member, when the elongate cylindrical member is in an extended position beyond the distal end of the tubular member.

7. A method for treating or preventing a vascular disease comprising:
    inserting a catheter into a blood vessel of a patient; and
    introducing a bioactive agent formulation into the blood vessel through the catheter,
    wherein the catheter comprises:
        an elongate tubular member comprising a proximal end, a distal end and a lumen extending from the proximal end to the distal end; and
        an elongate cylindrical member disposed at least partially within the lumen of the elongate tubular member and having a proximal end, a distal end and a delivery assembly extending from the distal end, wherein the delivery assembly comprises a lumen within the elongate cylindrical member that opens to a plurality of tubular channels which cumulatively release the bioactive agent formulation into the blood vessel, wherein the tubular channels are embedded within a wall of a flared conical shaped member of the delivery assembly, and outlets of the tubular channels, from which the bioactive agent formulation is released, are formed in the wall and face in a distal direction away from the distal end of the elongate tubular member.

8. The method according to claim 7, wherein the viscosity of the bioactive agent formulation is modified by an excipient comprising a polymer, a protein, a sugar or an alcohol.

9. The method according to claim 7, wherein introducing the bioactive agent formulation into the blood vessel of a patient does not impede the flow of blood through the vessel.

10. The method according to claim 7, wherein the bioactive agent formulation comprises a corticosteroid, everolimus, zotarolimus, sirolimus, a sirolimus derivative, paclitaxel, a bisphosphonate, ApoA1, a mutated ApoA1, ApoA1 milano, an ApoA1 mimetic peptide, an ABC A1 agonist, an anti-inflammatory agent, an anti-proliferative agent, an anti-angiogenic agent, an antifibrotic agent, a profibrotic agent, an antithrombotic agent, a matrix metalloproteinase inhibitor or a tissue inhibitor of metalloproteinase.

11. The method according to claim 7, wherein the bioactive agent formulation has a viscosity higher than that of blood and no greater than 500 centipoise.

12. The method of claim 11, wherein the viscosity of the bioactive agent formulation is no greater than 50 centipoise.

13. The method of claim 7, wherein the tubular channels are adjacent to an atherosclerotic lesion when the bioactive agent formulation is released from the tubular channels.

14. The method of claim 7, wherein the tubular channels are adjacent to a site of vulnerable plaque when the bioactive agent formulation is released from the tubular channels.

15. The method of claim 7, wherein when the bioactive agent formulation is released from the tubular channels, the tubular channels are adjacent to a site where angioplasty or another surgical procedure was previously performed.

* * * * *